United States Patent [19]

Choay

[11] 4,007,266
[45] *Feb. 8, 1977

[54] PHARMACEUTICAL COMPOSITION CONTAINING VITAMIN $B_{12}$, PROCESS OF MAKING THE SAME AND METHOD OF TREATMENT

[75] Inventor: Jean Choay, Neuilly-sur-Seine, France

[73] Assignee: Choay S.A., Paris, France

[ * ] Notice: The term of this patent subsequent to April 8, 1992, has been disclaimed.

[22] Filed: Feb. 26, 1975

[21] Appl. No.: 553,434

Related U.S. Application Data

[60] Division of Ser. No. 264,752, June 21, 1972, Pat. No. 3,876,765, which is a continuation-in-part of Ser. No. 820,296, April 29, 1969, abandoned, and a continuation-in-part of Ser. No. 820,297, April 29, 1969, abandoned.

[30] Foreign Application Priority Data

May 3, 1968 France ........................... 68.150415
May 3, 1968 France ........................... 68.150416

[52] U.S. Cl. .............. 424/105; 424/180; 424/201; 424/319
[51] Int. Cl.² .............. A61K 31/48; A61K 31/68; A61K 31/70; A61K 31/195
[58] Field of Search .......... 424/105, 180, 201, 319

[56] References Cited

UNITED STATES PATENTS 2,579,679  12/1951  Leffler ........................... 424/101

FOREIGN PATENTS OR APPLICATIONS 1,096,225  1/1955  France ........................... 424/95

OTHER PUBLICATIONS

Chem. Abst., I, 45, 9683f (1951).
Chem. Abst., II, 66, 1541g (1961).

*Primary Examiner*—Stanley J. Friedman
*Attorney, Agent, or Firm*—Michael J. Striker

[57] ABSTRACT

A pharmaceutical composition for the treatment of disorders in the formation or regeneration of the cutaneous connective tissue including disorders due to aging of the skin, which composition comprises a homogeneous mixture of vitamin $B_{12}$ in an amount effective for the above treatment and a carrier vehicle therefor. The carrier vehicle is a fatty skin cream of a pH between about 4 and 7 which is non-oxidizing and non-reducing and is pharmaceutically acceptable for repeated applications to the skin over prolonged periods of time.

11 Claims, 1 Drawing Figure

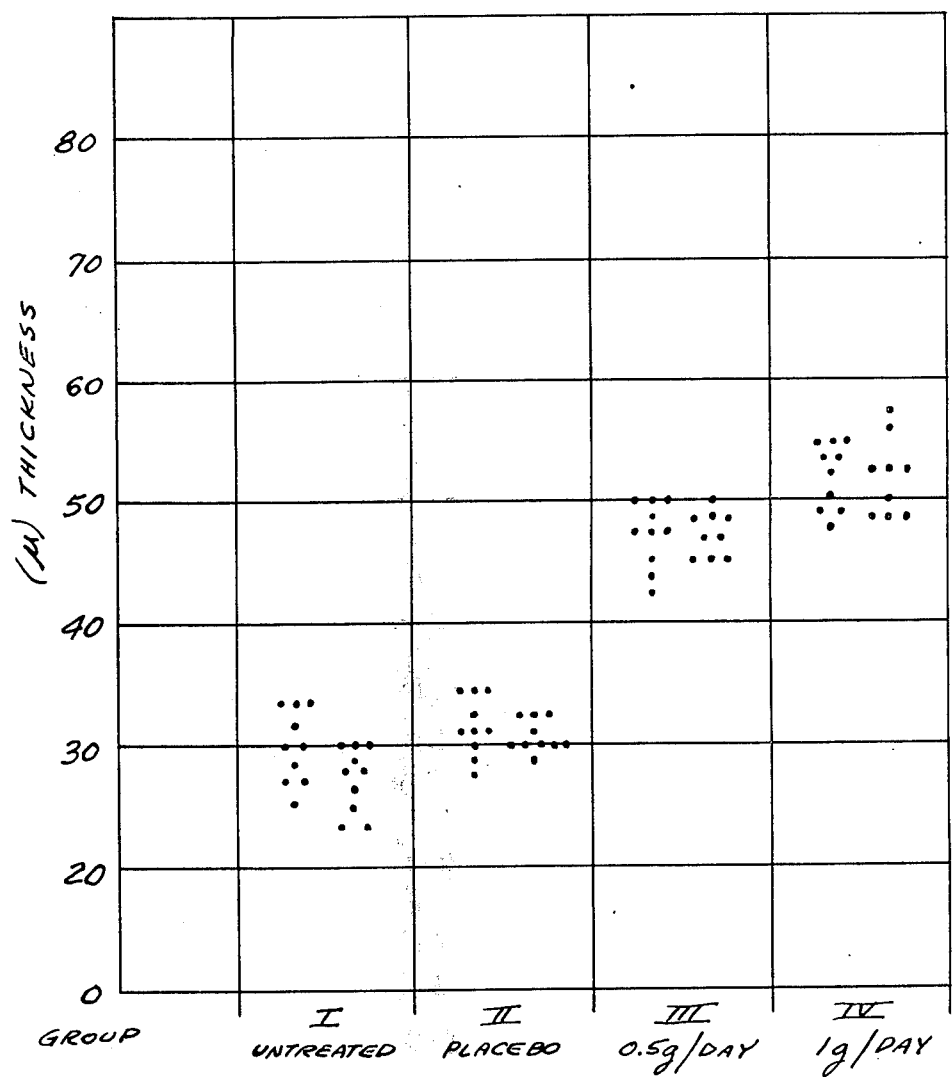

PHARMACEUTICAL COMPOSITION CONTAINING VITAMIN $B_{12}$, PROCESS OF MAKING THE SAME AND METHOD OF TREATMENT

CROSS-REFERENCES TO RELATED APPLICATIONS

The present application is a division of application Ser. No. 264,752 which in turn was a continuation-in-part of application Ser. No. 820,296 filed on Apr. 29, 1969 in respect of Novel Composition of the Treatment of Trophic Disorders of the Integuments, and application Ser. No. 820,297 filed on the same day in respect of Novel Cosmetics Containing Vitamin $B_{12}$. Applications 820,296 and 820,297 have now been abandoned. Application 264,752 has resulted in U.S. Pat. No. 3,876,765.

BACKGROUND OF THE INVENTION

The present application relates to a composition for the treatment of so-called trophic disorders of the teguments, that is, disorders in the production of the connective tissue fibers, particularly collagen and elastin. These disorders include the disorders due to aging of the skin with its accompanying reduction of cross-section and loss of elasticity as well as atrophic scleroses.

Cyanocobalamine or vitamin $B_{12}$ is an erythropoietic agent first isolated from the liver by Rikes et al. in this country and then by Smith in Great Britain. It has since been obtained on a commercial scale by starting with the metabolic products of certain microorganism and more specifically of the organism *Streptomyces Griseus* and *Streptomyces Aureofaciens* (Remington's Pharmaceutical Sciences 1965, page 1104).

Vitamin $B_{12}$ is a crystalline substance of an intense red color. It is identified either by its absorption spectrum (cf. USP XVII, page 153) or by its activity as growth factor in regard to microorganisms such as cultures of Lactobacillus *Lactis Dorner, L. Leichmannii* et *Euglena gracilis*.

It is normally stable in solution at a pH from 4 to 7 but is nevertheless unstable in the presence of oxidizing or reducing agents. Sunlight destroys it rapidly. A light intensity of 8,000 candle power causes its activity to go down by 10% for each period of 30 minutes. In red light however no destruction has been observed.

The metabolic activity of vitamin $B_{12}$ is high. It is particularly well known as erythropoietric factor. It has an anabolic action in connection with the protein metabolism and is effective as a growth factor. It is furthermore a lipotropic factor which activity is interconnected with its relation the methionine and choline.

In addition it acts as an antitoxicity factor concerning the effects caused by thyroxine and acts also as a neurotropic factor.

The major clinical uses of vitam $B_{12}$ are: Biermer anemia and the para-Biermer anemias which are cobalamino-curable, further neuritis and polyneuritis and disorders of the protein metabolism.

Vitamin $B_{12}$ is administered through the general constitutional system, particularly by way of injection and sometimes orally.

It is effective in dosages of microgram magnitude.

Although vitamin $B_{12}$ has not so far been administered by topical application it has been proposed to apply it by a percutaneous administration. This still is an adminstration in which the vitamin $B_{12}$ is rapidly diffused in the organism in a general constitutional manner without exercising a topical action. In this case the vitamin $B_{12}$ has been used as a solution in dimethyl sulfoxide (DMSO). It is noted in this connection that DMSO is a solvent which would have numerous shortcomings under the aspect of a topical therapeutic use. Under these conditions the tolerance for the drug is not very good. Furthermore, the speed of penetration of the skin of this carrier is high and therefore does not permit the effective agent to remain in contact with the tissues of the skin during an adequate time to cause the therapeutical action to take hold.

The applicant now has found that vitamin $B_{12}$ in one of the forms usually employed for therapeutical purposes such as cyanocobalamine or hydroxycobalamine can be topically applied if it is administered in a suitable vehicle which permits the desired limited percutaneous penetration.

SUMMARY OF THE INVENTION

The invention accordingly resides in a pharmaceutical composition for the treatment of the indicated disorders which comprises a homogeneous mixture of vitamin $B_{12}$ in an amount effective for such treatment together with a carrier vehicle therefor which latter is a fatty skin cream of a pH between about 4 and 7 which is nonoxidizing and nonreducing and is pharmaceutically acceptable for repeated applications to the skin over prolonged periods of time.

BRIEF DESCRIPTION OF THE DRAWING

The drawing shows the different thicknesses of the skin appearing in four groups of rats, the scale expressed in microns and the four groups comprising the control group which was not subject to any treatment (I), a group II to which the same composition was administered as to groups III and IV which however did not contain vitamin $B_{12}$ and the groups III and IV to which amounts of 500 mg/day (group III) and 1 g/day (group IV) were administered for a period of 4 weeks with one administration per day for 6 days of each week, the composition being further specified below.

DETAILS OF THE INVENTION AND PREFERRED EMBODIMENTS

The compositions of the invention are in the form of creams, pomades or unguents or similar. Their action is in particular in respect of damaged or injured skin due to cessation or impairment of the production of the fibers of the cutaneous connective tissue. The action of the compositions consists in a stimulation of fiber production and particularly in a rebuilding of the network of elastin fibers wich form part of the connective tissue. The action is equally applicable to cases where the affected production of the connective tissue fibers due to an accidental injury and to those cases where it is due to the process of natural aging.

This action of a reconstitution of the cutaneous fibers was unexpected and surprising since the vitamin $B_{12}$ was known only as an antianemia factor. The applicant has found that the stimulation of the production of connective tissue fibers obtained by the composition of the present invention is due to the action of the vitamin $B_{12}$ on the activity of the fibroblasts.

This unusual effect on the skin can be obtained because of the association of vitamin $B_{12}$ with a suitable vehicle. The choice of a percutaneous penetration vehicle which must be associated with the vitamin $B_{12}$ has significant importance since it is this vehicle which must retain or retard the vitamin $B_{12}$ at the dermo-epidermic junction and which thus permits the effective agent to act on the injured or damaged skin by stimulation of the production of the connective fiber tissues.

Apart from the suitability to retain the vitamin $B_{12}$ for a sufficient period of time at the dermo-epidermic junction and to prevent its diffusion through the general systemic ways the vehicle which is associated with the vitamin $B_{12}$ must have a number of additional properties:

It must in particular with the vitamin $B_{12}$ form a homogeneous mass, stable over long periods of time so as not to cause a salting out of the vitamin. Furthermore because of the great sensibility of the vitamin $B_{12}$, particularly in regard to oxidizing and reducing agents at a pH below about 4 and above about 7, and considering its solubility in an aqueous phase and its tendency to undergo modifications due to the action of light, the vehicle must be completely compatible with vitamin $B_{12}$ which must not be altered by it. This means that the cream, pomade or similar according to the invention must have a pH between about 4 and 7 and must be free of oxidizing and reducing properties. The vehicle must furthermore be adapted to form a cream, pomade, or similar which can be applied to the skin. The tolerance for it therefore must be high even at extended daily applications for periods such as several months or even years.

For this purpose various lipidic compositions in cream form which are available on the market and which are well known as cosmetic preparations can be used. Many of these creams are listed in the standard reference work "Kosmetologie" by J. S. Jellinek (1959 edition).

Illustrative are for instance the following fatty creams which can be employed as carriers for the vitamin $B_{12}$.

1. A mixture of fatty acids of 8 to 28 carbon atoms which forms a self-emulsifying mass in water, such as, the commercially available cream sold under the trademark "Xalifin 15" by the Vevy Company of Genoa, Italy, which as indicated by the manufacturer ("Relata Vevy", Supplement No. 2, 1965) comprises the following acids, preferably in the amounts stated herewith in weight percentages and subject to slight adjustments since the total does not add up to 100%:

| Oleic | about | 26 % |
|---|---|---|
| Linoleic | " | 44 % |
| Palmitic | " | 19 % |
| Stearic | " | 8 % |
| Arachic | " | 4 % |
| Myristic | " | 0.40% |
| Myristoleic | " | 0.20% |
| Heptadecanoic | " | 1.90% |
| Linolenic | " | 1.20% |

2. Mixtures of mono- and diglycerides of saturated fatty acids, particularly, palmitic and stearic acid. This cream is commercially sold under the trademark "CUTINA MD" by the Henkel and Co. GmbH of Dusseldorf, Federal Republic of Germany.

3. Polyoxyethylene glycol ethers of fatty alcohols having 16, 18 and 20 carbon atoms. The alcohols are preferably ethoxylated to a degree between 67 and 69%. Creams of this type are sold under the trademark "Eumulgin C 700" by the Henkel Company mentioned in the previous item.

4. High molecular alkyl side chain substituted primary aliphatic alcohols obtained by condensation by the Guerbet method. Examples are hexyldecanol, decyldodecanol and hexyloctadecanol. These products are described in French Pat. No. 1,089,353 and sold by the Henkel company mentioned in item 2 under the name "Eutanol G".

5. Mixtures of mono- and distearates of polyoxyethylene glycols with an average molecular weight of about 600. This type of product is sold by the Gattefosse company of Boulogne-sur-Seine, France under the trademark "Tefose 1500". A similar product consists of a mixture of palmitic and stearic mono- and diesters of polyoxyethyleneglycol of an average molecular weight of about 300, such as, the product sold by the Gattefosse company under the trademark "Polystate", see Pharmacopee Francaise, 8th Edition, page 833.

6. A similar product are the stearic monoesters of sorbitan polyoxyethylene glycol sold as "Tween 61" by the Atlas Powder Company.

7. Mixtures of higher fatty alcohols, particularly equal parts of cetyl and stearyl alcohol. A product of this type is sold under the trademark "Lanette O" by the Henkel company mentioned in item 2 above.

8. Compositions on the basis of mixtures of oleic and stearic esters of propylene glycol and of mixtures of oxyethylenated oleic and cetyl alcohols, such as sold under the trademark "Hydrolactol 61" by the Gattefosse company mentioned in item 5 above.

9. Mixtures of esters of saturated fatty acids which have alkyl side chains, such as the product "PCL-Solid" sold by the Dragoco company.

These various lipidic carrier vehicles can either be used singly or in combination. Preferably various vehicles are used conjointly for example "Cutina MD" and "Eumulgin C 700" are used together or "Eutanol G" is used with "Cutina MD" and "Emulgin C 700" or "Tefose 1500" with "Polystate" or "Lanette O" with "Eumulgin C 700". The properties in these combined carrier vehicles supplement each other when associated with vitamin $B_{12}$.

According to preferred embodiments the cream or pomade is associated additionally with other substances or compounds which have synergistic effects regarding the disorders of the production of the connective tissue fibers.

According to a first embodiment it is preferred to use the vitam $B_{12}$ in one of the above vehicles together with ribonucleic acid.

Another embodiment of the invention is the combined use of the lipidic vehicle, vitamin $B_{12}$ and an embryo extract such as an extract of chicken embryos. According to a third preferred embodiment the combination includes N-propionyl-$\epsilon$-amino-caproic acid or one of its soluble salts, specifically, sodium, calcium or magnesium salt. This compound and a process of making are described in application Ser. No. 104,495 filed by the same inventor on Jan. 6, 1971 and forming a division of application Ser. No. 820,298 filed Apr. 29, 1969.

The formula of N-propionyl-$\epsilon$-amino-caproic acid is $CH_3CH_2—CO—NH—(CH_2)_5—COOH$. The acid is prepared by reaction between propionic acid anhydride

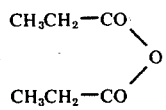

and ε-amino-caproic acid.

Among the salts of N-propionyl-ε-amino-caproic acid, only sodium, calcium and magnesium salts have been isolated.

The sodium salt of N-propionyl-ε-amino-caproic acid is a compound having the formula $CH_3-CH_2-CO-NH-(CH_2)_5-COONa$, the molecular weight of which is 209.23, and m.p. is of the order of 199° to 200° C; it has the appearance of a white powder soluble in water and alcohol, insoluble in ketone and ether.

The calcium salt of N-propionyl-ε-amino-caproic acid is a compound having the formula $[CH_3-CH_2-CO-NH-(CH_2)_5-COO]_2Ca$, a molecular weight of 412.55 and a m.p. of the order of 179° to 182° C; it has the appearance of a white powder soluble in water and alcohol, insoluble in ketone and ether.

The magnesium salt of N-propionyl-ε-amino-caproic acid is a compound having the formula $[CH_3-CH_2-CO-NH-(CH_2)_5-COO]_2 Mg$, and a molecular weight of 396.80; it has the appearance of a white powder soluble in water and alcohol, insoluble in ketone and ether.

The chicken embryo extract is obtained by placing chicken embryos in a sodium chloride solution in amounts of 1,000 chicken embryos for 1,000 ml of sodium chloride. There is thus obtained a solution of 1 ml which corresponds to 1 gram of embryo extract. This type of process is further described in R. C. Parker, "Methods of tissue culture", 3rd Edition, New York, 1962, page 102 etc. Preferably the vitamin $B_{12}$ is present in the cream in amounts between 1 and 100 micrograms.

The synergistically active substances are preferably present in the following amounts if added to the composition:

0.25 to 1 mg per gram of total cream in the case of ribonucleic acid; 0.005 to 0.025 ml per gram of cream in the case of the chicken embryo extract; and 10 to 50 mg/g of cream in case of the N-propionyl-ε-amino-caproic acid and the same applies to the salts of the acid.

The compositions may however include still further additives in the form of nutritive additives for the cutaneous tissue such as vegetable oils, perhydrosqualene ($C_{30}H_{62}$) (sold under the trademark "Cosbiol" by the Laserson et Sabetay company of La Garenne-Colombes, France; see Pharmacopée Française, 8th Edition, page 789). Likewise preservatives may be added and if desired fungicidal agents or (and) antioxidants such as tocopherol acetate may be added. Likewise perfuming agents may be included.

A process of preparing the cream preferably is as follows. An aqueous phase containing the vitamin $B_{12}$ is prepared in form of an aqueous solution. Separately a lipidic phase is prepared containing the percutaneous penetration vehicle. The two phases can be prepared at an elevated temperature, preferably, at a temperature between 40° and 60° C. They are then mixed upon agitation and finally cooled to about 30° to 40° C. After that they are subjected to the action of a homogenizer to obtain a pomade, cream or similar.

The entire process of making the cream must be carried out protected by light in order to avoid the destruction of the vitamin $B_{12}$. The synergistically active substances may be introduced either in the aqueous or in the lipidic phase depending on their chemical nature.

The following examples illustrate the compositions of the invention. Some of the fatty carrier vehicles have been identified only by trademarks. The more specific meaning of these trademarks has been given in the above discussion. It is noted that all of these trademarked fatty cream components are well known in the trade and generally used for cosmetic and related pharmaceutical purposes.

EXAMPLE 1

This example relating to a specific composition will also illustrate the making of the composition. Insofar as the process aspects are concerned these apply in a similar manner to the other examples where different compositions are discussed.

On the one hand an aqueous phase was prepared containing the vitamin $B_{12}$ while on the other hand there was prepared a lipidic phase containing the penetration vehicle. Regarding the amounts used reference is made to the composition set out below. The two phases were prepared by heating the solutions or emulsions to between 40° and 60° C. The two phases were then mixed upon agitation and finally cooled to about 30° and 40° C. The total mass was then passed, after cooling, to a homogenizer in order to obtain a cosmetic composition.

All operations were carried out sheltered from light in order to avoid destruction of the vitamin $B_{12}$.

The penetration carrier vehicle used in this case was a lipidic substrate constituted essentially by nine fatty acids which form a self-emulsifying mass in water. Thus the addition of separate surface active agent was not necessary.

The cream used in this example had the following composition:

| Lipidic phase: | "Xalifin 15" | 27 g |
|---|---|---|
| | Perhydrosqualine ("Cosbiol") | 10 g |
| Aqueous phase: | Vitamin $B_{12}$ in the form of cyanocobalamine (hydroxy-cobalamine could also be used | 0.001 g |
| | Sorbic acid as preservative perfume — a few drops | 0.2 g |
| | Water (q.s.) | 100 g |

EXAMPLE 2

The carrier vehicle used in this example was not a self-emulsifying composition and had therefore to be used in association with an emulsifying agent in order to prepare a proper emulsion of the water in oil emulsion type.

| Lipidic Phase | | |
|---|---|---|
| Penetration agents: | "Cutina MD" | 13 g |
| | "Eumulgin C 700" | 3 g |
| Nutritive substances: | Vegetable oils | 8 g |
| | White wax (white bees wax) | 1 g |
| | "Cosbiol" | 5 g |
| | Lanolin Oil (sold under the trademark "Ritalan" by | |

-continued

| | | |
|---|---|---|
| | the Gattefosse Company | |
| Boric acid | | 3 g |
| Triethanolamine | | 0.2 g |
| Aqueous Phase | | 1 g |
| Active substance: | Vitamin $B_{12}$ | 0.001 g |
| Preservatives: | Sorbic acid | 0.2 g |
| | Sorbitol | 5.0 g |
| Hamamelin water | (witch hazel) | 5.0 g |
| | Perfume q. s. | |
| | Water (q.s.) (deionized) | 100.0 g |

The composition was formed in the same manner as the composition of Example 1.

EXAMPLE 3

The vehicles used in this example were emulsions of the oil in water emulsion type. They were nonionic substances which included an emulsifier in order to be dispersible in the water.

The following is the composition used in this example:

| Lipidic Phase | "Tefose 1500" | 5 g |
|---|---|---|
| | "Polystate" | 2 g |
| Nutritive substances: | Vegetable oil | 3 g |
| | "Cosbiol" | 6 g |
| Aqueous Phase | | |
| Active substance: | Vitamin $B_{12}$ | 0.001 g |
| | Sorbic acid as preservative | 0.4 g |
| | Water (q.s.) (deionized) | 100 g |

To make this composition the same method was used as in Example 1.

EXAMPLE 4

The vehicles used in this example are of the water in oil emulsifying and wetting type. The composition was as follows:

| Lipidic Phase | | |
|---|---|---|
| Carrier vehicle for percutaneous penetration: | | |
| | "Lanette O" | 10 g |
| | "Eumulgin C 700" | 3.5 g |
| Nutritive additives: | "Ritalan" (see Example 2, lanoline oil) | 4 g |
| | "Cosbiol" (in place of which a vegetable oil could also be used | 4 g |
| Aqueous Phase | | |
| Active substance: Sorbic acid as preservative: | Vitamin $B_{12}$ | 0.001 g |
| | | 0.4 g |
| | Water (q.s.) | 100 g |

EXAMPLE 5

The vehicles used in this example, particularly "Hydrolactol" are of the self-emulsifying type. The composition was as follows:

| Lipidic Phase | | |
|---|---|---|
| Percutaneous penetration vehicle: | | |
| | "Hydrolactol 61" | 12 g |
| Nutritive substances: | "Ritalan" (lanoline oil) | 5 g |
| | "Cosiol" (or vegetable oils) | 5 g |
| Aqueous Phase | | |
| Active substance: | Vitamin $B_{12}$ | 0.001 g |
| Preservative | Sorbic acid | 0.4 g |
| | Water (q.s.) | 100 g |

The compositions preferably are made as described in Example 1.

EXAMPLE 6

A composition was prepared as in Example 1 in which however the aqueous phase in addition to the Vitamin $B_{12}$ also contained an amount of 1 ml of chicken embryo extract.

EXAMPLE 7

A composition was prepared as in Example 1 in which however the aqueous phase in addition to the vitamin $B_{12}$ also contained 25 mg of ribonucleic acid.

EXAMPLE 8

A composition was prepared as in Example 1 of which however the aqueous phase in addition to the vitamin $B_{12}$ also contained N-propionyl-ε-aminocaproic acid in an amount of 1 g.

EXAMPLE 9

A cream was prepared of the following composition:

| | |
|---|---|
| Vitamin $B_{12}$ | 0.010 g |
| "Cutina MD" | 13 g |
| "Eumulgin C 700" | 2 g |
| "Eutanol G" | 7 g |
| Avacado oil | 8 g |
| Lanolin oil ("Ritalan") | 3 g |
| White wax (white bees wax) | 1 g |
| Perhydrosqualene ("Cosbiol") | 5 |
| Stearic acid | 0.2 g |
| Sorbitol | 5 g |
| Triethanolamine | 1 g |
| Hamamelis water (witch hazel) | 5 g |
| Sorbic acid | 0.2 g |
| Tocopherol acetate | 0.1 g |
| Water (q.s.) (deionized) | 100 g |

EXAMPLE 10

A cream was prepared with the following composition:

| | | |
|---|---|---|
| Vitamin $B_{12}$ | 0.010 | g |
| Ribonucleic acid | 0.10 | g |
| Sorbic acid | 0.40 | g |
| Perhydrosqualene ("Cosbiol") | 10 | g |
| "Xalifin 15" | 27 | g |
| Water (q.s.) (deionized) | 100 | g |

EXAMPLE 11

A cream was prepared of which the composition was as follows:

| | | |
|---|---|---|
| Vitamin $B_{12}$ | 0.010 | g |
| Chicken embryo extract | 2.5 | ml |
| Sorbic acid | 0.4 | g |
| Perhydrosqualene ("Cusbiol") | 10 | g |
| "Xalifin 15" | 27 | g |
| Water (q.s.) (deionized) | 100 | g |

EXAMPLE 12

A composition was prepared as follows:

| | | |
|---|---|---|
| Vitamin $B_{12}$ | 0.010 | g |
| N-propionyl-amino caproic acid | 5 | g |
| Sorbic acid | 0.4 | g |
| Perhydrosqualene ("Cosbiol") | 10 | g |
| "Xalifin 15" | 27 | g |
| Water (q.s.) (deionized) | 100 | g |

It will be understood that other vehicles could also be used provided they had the necessary tolerance properties, the necessary penetration properties and compatibility with vitamin $B_{12}$.

UTILITY

The following tests including pharmacological and pharmacodynamic studies show the use of the compositions of the invention and their action in connection with the treatment of the production of connective tissue fibers.

Animal Tests: Ultraviolet Burns

These tests were carried out with rats. A portion of the skin on the back of the rat was depilated and then exposed to ultraviolet radiation produced by an MLH 300 W Philips lamp during 10 min. at a distance of 50 cm between the source of the radiation and the animal. There was thus obtained an erythema type solar burn. The animals were then divided into two groups of which the first group was subjected to the treatment with the compositions of the invention while the other group was used as control group. The burn was then treated by applying a cream of the invention further identified below in an amount of 1 g/day. The application was effected twice a day during four consecutive days. The composition was that described in Example 9 above.

The skin of the animals treated with the composition of the invention quickly resumed its normal appearance and rapid disappearance of the phlyctanae could be observed while the scaling (desquamation) diminished. In the animals of the control group these improvements were not observed.

Animal Tests: Aging Phenomena

These tests were also carried out with rats, specifically with old rats in which the skin was characterized by a lack of cross-sectional thickness and a reduction of the natural elastic properties.

This reduction of cross-sectional thickness that is the thinning out of the skin is caused by a reduction in the regeneration capacities of the basal cells of the epidermis.

The reduction of the elasticity of the teguments is caused by changes in the network of the elastin fibers which are located in the area of the dermo-epidermic junction. In old rats the elastin fibers are heavy and fragmentized which results in a reduction of their elastic properties.

One can likewise observe a distinct reduction of the production of muco-polysaccharides by the cells of the dermis. The muco-polysaccharides constitute one of the essential elements of the basic connective tissue substance.

The collagenous protein fibers furthermore are thick and hardened.

These three elements, the changed character of the elastic fibers, the lower production of muco-polysaccharides and the changed characters of the fibrillary collagen result in the decreased elasticity and suppleness of the cutaneous covering.

Rats are used herein for the pharmacological and pharmacodynamic tests because there exists a correlation between the skin of old rats and the aged human skin. Actually the elastin network of the back skin of rats was found to be absolutely identical with that of the human skin and the thickening of the collagen fibers and fibrils occurs in the same way in the skin of old rats as in the skin of aged human beings.

The tests have been undertaken for the purpose to measure the effects of the local application of vitamin $B_{12}$ in imparting a normal activity to the cells of the epidermis and to the fibroblasts of the dermis resulting in a slowing down of the degenerative senility process. The problem in this approach essentially is to permit the vitamin $B_{12}$ to penetrate the barrier of the epidermis without passing entirely through the dermis so as to obtain a high vitamin concentration in the dermo-epidermic transition zone.

The tests regarding elasticity of the skin were carried out with old male Wistar rats which were strictly controlled from their issue throughout their growth. The tests were effected on rats which were 30 months old and were brought up under rigorously identical conditions.

In the back area of the skin histological examinations showed that the dermis was comprised of a network of elastin fibers which were longitudinally oriented in a direction from head to tail parallel to the spinal column. The skin can therefore be stretched in the direction of the elastin fibers and the elongation will be as much greater and easier as the subject animal is younger.

To carry out the tests a skin strip of 3 cm length and 0.50 cm width was cut out parallel to the axis of the spinal column. The strip was then held at the neck end in a stationary hold. At the other end, the tail end, a force of 50 g was applied during 5 minutes. The length of the cutaneous strip was measured after 5 minutes of traction without releasing the stretching force.

These test thus permits to determine the possibilities of stretching and therefore the elasticity of the cutaneous covering. In the young subject animal an elongation is obtained which is much greater than that in the aged rat.

The histological study of the skin was carried out on a sufficiently large specimen of the teguments of the cutaneous back zone which was treated with applications of the vitamin $B_{12}$ cream of the invention. The specific composition of the applied cream will be given below.

There were then observed the thickness of the epidermis, the presence of ribonucleic acid in the basal cells of the epidermis, the structure of the different fibrillary elements of the dermis, such as collagen and elastin fibers, and the presence of muco-polysaccharides in the dermis.

The specimens were preserved with a Carnoy fixative or with neutral formal solution depending on the specific technique applied. The specimens were enclosed in paraffin prior to being cut up.

The thickness of the epidermis was measured on colored slices by the Manon technique. The measurements were determined microscopically (lens: × 40, eye piece: × 10). The values were the mean of 20 measurings carried out on each slide.

The ribonucleic acid of the basal layer was dyed by reaction with toluedine blue at a pH of 3.

The connective tisue of the dermis was colored by the technique of Masson, of Van Gieson and of Mallory. The specific color permitted a clear observation of the collagen fibers.

The elastin fibers were identified by dying according to Weigert with fuchsine-resorcinol and by dying according to Gomori with aldehyde-fuchsine. Whether the reactions were positive was determined by the action of the pancreatic elastase.

The presence of muco-polysaccharides were determined by the Hale reaction.

The histochemical reactions were obtained and observed on several slides taken from the same specimen. On each slide several areas were examined. The reaction is so much more intense as the tissue is richer in the component that forms the subject of the specific study. This examination permits to obtain information of a qualitative order which is not absolute but must be interpreted as a function of the corresponding results obtained with slides from the control groups.

The cream employed in these tests was the same as described above in Example 9 except that the stearic acid was replaced by boric acid. In addition, in a separate group a placebo cream was applied which had likewise the composition described in Example 9 in which the same replacement of acid was made but in which the vitamin $B_{12}$ was omitted. In addition there was a control group of animals which did not receive any treatment at all.

The dosage was as follows. The skin was first depilated with a cosmetic wax whereupon daily the following amounts of cream were applied: 500 mg to one group of rats and 1 g to another group. The application was carried out once a day for 4 weeks. In each week the cream was applied on 6 days only.

The placebo cream was applied under exactly the same conditions of administration.

The rats employed as subject animals were as already noted Wistar male rats of identical age (30 months) and of comparable weight (400 to 480 g). The animals were kept under the identical conditions of kenneling and received the same synthetic elementation (type "U.A.R."). The animals were then divided into lots of 10 animals each. 20 rats were used in the control group.

For each rat there were determined:
a. The elasticity of the skin specimen observed in an autopsy.
b. The thickness of the epidermis and the histo-chemical characteristic observed in histological slides.

More specifically 20 rats were administered 500 mg of the cream of the invention per day, another group of 20 rats were administered 1 g of the cream of the invention per day and a third group of 20 rats received 1 g of the placebo cream per day.

The animals were then sacrificed by decapitation after 4 weeks of treatment. The elasticity of the skin was immediately measured in the manner above described.

All tests were carried out blind; the laboratory personnel did not know the composition of the creams.

The histological slides were likewise interpreted by blind tests.

a. Findings in old not treated rats.

The following table shows the elasticity of the back skin of rats in groups of 10 subject animals of more or less identical weight which had not received any treatment:

TABLE I

| Weight of Animals | Mean Elongation | % Elongation (*) |
|---|---|---|
| 400 g | 60 mm ± 12 | + 20 |
| 480 g | 70 mm ± 12 | + 23 |

(*)The percentage elongation is determined in relation to the length of the skin strip as it existed at the moment of separation (30 mm).

The thickness of the epidermis was measured in microns by means of the graduation on the eye piece of the microscope. The results appear from the attached drawing. The individual results are indicated by dots. The group I is the control group, group II is the group treated with the placebo cream, group III is the group treated with 500 mg of the cream of Example 9 per day, and group IV is the group treated with 1 g of the same cream per day.

The histological and histochemical studies showed the following: The cells of the basal layer of the epidermis were faintly colored by the toluene blue at a pH of 3. Frequently the reaction was even completely negative which indicated the absence of ribonucleic acid in the cytoplasm of the cells. On the other hand there was no indication of a mitosis (cell division) phenomenon.

The connective tissue of the dermis was characterized by a substantial thickening of the collagen fibers, and the breaking up and fragmentation of the elastin fibers. The Hale reaction was faintly positive which indicated a weak production of mucopolysacchrides.

These histological characteristics are those of a senile skin.

In conclusion it was found that the skin of old rats had little elasticity, that the epidermis was thin, that in the dermis the collagen fibers were thickened while the elastin crosswork was disorderly and the reaction for identification of the mucopolysacchardies was faintly positive.

b. Results obtained with old rats which were treated with the placebo cream

The elasticity of the skin of the back was tested with groups of 10 subject animals. The animals received 1 g of the cream above-identified per day for the period above-identified. The results appearing from the following Table II.

TABLE II

| Weight of Animals | Mean Elongation | % Elongation |
|---|---|---|
| 450 g | 62 mm ± 11.5 | + 20 |
| 470 g | 75 mm ± 15.2 | + 25 |

The results appearing from Table II are accordingly practically identical with those in the control group.

The results regarding thickness of the epidermis appear again from the drawing where group II is the group which received the placebo cream. As the drawing shows, the epidermis of the subject animals was as thin as that of the control group.

The histological and histochemical tests were carried out in the same manner as with the slides obtained from the control groups. There was again found a thickening of the collagen fibers and a disorganized state of the network of elastin fibers.

The Hale reaction was faintly positive.

c. Results obtained with old rats treated with the composition of the invention

The determination of the elasticity of the back skin of the rats as carried out in the manner above described appears from the following Table III.

TABLE III

| Weight of Animals | Mean Elongation | % Elongation |
|---|---|---|
| Group III | | |
| 480 g | 110 m ± 11.5 | + 36 |
| 475 g | 114 mm ± 10 | + 38 |
| Group IV | | |
| 450 g | 124 mm ± 15 | + 40 |
| 465 g | 160 mm ± 12 | +53 |

Accordingly one observes a strong increase of the elasticity of the teguments in both of these groups relative to the results obtained with the control groups. The percentage elongation is quite similar in both treated groups.

The dosage applied in these cases was 0.50 g/rat per day and accordingly this dose clearly leads to an increase of the elasticity of the skin.

Regarding the thickness of the epidermis reference is again made to the attached drawing in which groups III and IV are the groups treated with the cream of the invention. As appears the epidermis is considerably thicker than in both control groups.

Insofar as the histological and histo-chemical tests are concerned they show in the area of the epidermis that there is a substantial thickening of the epidermis discernible particularly in the layer of the basal cells. Also numerous mitoses were observed. The cytoplasm of the cells was strongly colored by the toluidine-blue which indicated the presence of ribonucleic acid.

In the connective tissue area of the dermis the following findings were obtained.

The collagen fibers were less thickened than in the slides obtained from the control groups. They are submerged in a substance strongly dyed by the Hale reaction. This reaction is highly positive in the zone of the dermo-epidermic junction which indicates the metabolic activity of the connective cells in this area.

The elastin fibers form a fine and well organized network which extends throughout the dermo-epidermic zone. The elastin network is particularly well developed around the hair follicles. These facts likewise indicate the activity of the fibroblasts and presence of the mucopolysaccharides permitting the reorganization of the network of elastic fibers.

These facts are identical in groups III and IV of Table III (identified as groups III and IV also in the Drawing).

From these histological studies it can be concluded that due to the effect of vitamin $B_{12}$ the connective tissue cells and in particular the fibroblasts have resumed a strong metabolic activity favoring the synthesis of the essential constituents of the basic material which permits the reformation of the elastin network.

This activity is likewise discernible in the layer of the basal cells of the epidermis inasmuch as the cells are capable of division which in turn causes an increase in the thickness of the epidermis.

The pharmacodynamical tests thus lead to the conclusion that vitamin $B_{12}$ when applied in a percutaneous manner in a carrier vehicle which does not permit its passage through and beyond the dermis will increase the elasticity of the teguments, will operate in the direction of a reformation of the network of elastin fibers and in the production of thin and regularly composed collagen fibers. This action undoubtedly is provoked by the resumption of the normal metabolic activity of the basal cells of the epidermis and of the connective cells of the dermis.

HUMAN TESTS a. Solar Burns

These clinical tests were carried out in an alpine training camp located at high altitude. The camp was in a shelter house at 2600 m altitude in the Mont-Blanc range. Among the tested persons were youthful trainees, nonprofessionals, mountain guides, and instructors of the French Alpine Club.

The test results were recorded by the medical group of the camp. The test persons comprised three age groups, from 20 to 25 for the trainees, from 30 to 40 for the guides and from 30 to 36 for the instructors.

The injuries involved were superficiary injuries of the skin due to prolonged exposure to ultraviolet rays which of course abound in this high altitude. The injuries were aggravated by the climate, the time spent on glaciers, the wind and the extreme cold of the high altitude. The injuries were characterized by solar erythemas which were or were not accompanied by phlyctenas and scaling (desquamation). The skin of the mountain guides and instructors was dry, thick and quite wrinkled.

Habitually the Alpine climbers usually do not use conditioning creams but use only filtering products which they apply exclusively to the lips.

The cream used in these tests was that described in Example 10 above. The cream was applied upon return from the mountain trips to all those individuals which had injured skin portions. It was administered in two or three applications per day to the injured area. The results obtained appear from the following table.

TABLE I

| Age | Sex | Condition | Duration of Treatment | Results |
|---|---|---|---|---|
| 22 | M | Sunburn | 5 days | Rapid normalization, skin agains supple, scaling stopped. |
| 23 | F | Sunburn | 7 days | Improvement of burns, slight return of suppleness, normal moisture contents. |
| 30 | M | Sunburn | 5 days | Burning sensation improved, normal epidermis after 3 days of treatment. |
| 20 | F | Sunburn | 5 days | Burning sensation improved, normal epidermis after 3 days of treatment. |
| 25 | F | Sunburn scaling | 5 days | Scaling halted, increased softness of the skin. |
| 20 | F | Sunburn | 2 days | Improvement of burns. |
| 25 | F | Tanned, wrinkled, dried out | 5 days | The test person declared that her skin was softer, less dry. |
| 32 | M | dried out | 5 days | Gradual improvement of softness, diminishment of wrinkles, good protection for the lips. |
| 35 | M | Tanned, wrinkled, dried out plug lip protection | 5 days | Same results as in preceding test, softening of the skin of the hands. |
| 25 | M | wrinkled, dried out | 5 days | Same results as in preceding tests. Good protection for the lips. |
| 36 | F | wrinkled, dried out | 3 weeks | General softening of the skin. Improvements of the wrinkles. |
| 20 | F | Grave sun exposure | 3 days | Improvement of the burning phenomena and no more scaling. |
| 35 | M | Preventive | 1 application before trip, 1 application during trip | The protected parts remain soft (arms), the other parts undergo solar erythema. |
| 40 | M | Deeply tanned | Advance protective use for lips and face | No injury in spite of 10 hours stay on glacier in full sunlight. |

As appears the cream of the invention results in a very substantial reduction or rapid improvement of the injuries caused by ultraviolet rays as well as in a softening of the skin.

b. Wrinkles due to aging

The cream used in these tests had the following composition and was applied once daily for 7 weeks:

| | |
|---|---|
| Vitamin $B_{12}$ | 25 μg |
| "PCL-Solid" | 6 g |
| "Geleol" (mixture of mono-, di-, and triglycerides of stearic acid, a product of the Gattefosse company) | 3 g |
| "Tween 61" | 1.5 g |
| Cetyl alcohol (product of the Givaudan company, similar to "Lanette O") | 2 g |
| "Acetulan" (acetylated lanolin fractions, a product of the Petroles d'Aquitaine company, similar to "Ritalant") | 1 g |
| "HD Ocenol 50/55" similar to "Lanette O" but of lower grade of purity, product of the Henkel company) | 0.5 g |
| Preservative | 1.0 g |
| Water | 83 g |

In the first test the cream was used by 20 women. Regarding the cosmetic aspects of the cream only their subjective judgement is reproduced here. Without exception it was favorable on the following grounds: The cream could easily be spread, it was not too fatty and not too dry, it was rapidly absorbed and it left no shine on the skin.

The age of the test persons:

| | |
|---|---|
| 20 to 29 years | 3 persons |
| 30 to 39 years | 3 persons |
| 40 to 49 years | 10 persons |
| 50 to 59 years | 2 persons |
| above 60 years | 2 persons |

It appears therefore that all age groups were represented with the majority of the test persons being in the middle age group.

Likewise the test persons had all kinds of skin types: nine had dry skin, nine had intermediate skin, and two had oily skin; eight had dehydrated skin, eight had skin reddened by strong circulation and five had congested skin while six had wrinkled skin and one test person had a highly wrinkled skin.

The results obtained were evaluated by a biologically trained beautician and appear from the following Table V.

TABLE V

| | |
|---|---|
| Spectacular Improvement | 5 women |
| | 40 to 45 years 2 women |
| | 50 years 1 woman |
| | 57 years 1 woman |
| | 61 years 1 woman |
| | In all of these five women good mositure contents and a fresh looking skin was produced. |
| | In addition: |
| | For one woman there was an important tightening of the skin of the neck and of the oval of the face; |
| | For two women there was a tightening of the skin of the neck and of the oval of the face and furhermore a clear reduction of the depth of the wrinkles; |
| | For one woman the entire face was less tense in the appearance of the skin and for another woman the skin was more smooth and the wrinkles on the cheeks had disappeared. |
| Improvement less spectacular but nevertheless discernible | Seven women were tested in the following age groups: |

TABLE V-continued

| | |
|---|---|
| | 20 to 25 years 1 woman |
| | 25 to 30 years 1 woman |
| | 30 to 35 years 1 woman |
| | 45 to 50 years 2 women |
| | 55 to 60 years 1 woman |
| | above 60 years 1 woman |
| | For these seven women the skin in general had a satisfactory mositure content after application. |
| | In addition: |
| | For one woman the skin appeared more dense and the pores were closer (the skin was less oily); |
| | For one woman the grain structure of the skin was clearly improved, it had a less reddish appearance and the pores were less dilated; |
| | For one woman the face was tighter and more invigorated; |
| | For one woman there was a tightening of the skin of the neck and a higher elasticity of the tissues of the skin; |
| | For one woman there was a reduction of the wrinkles around the eyes and lips; |
| | For two women there was a tightening of the skin tissues around the neck. |
| Slight improvement | Eight women were examined in the following age groups: |
| | 20 to 25 years 1 woman |
| | 30 to 35 years 1 woman |
| | 40 to 45 years 4 women |
| | 45 to 50 years 2 women |
| | Moisture and elasticity of the skin tissues were improved. |

In summary the results of the application of the composition of the invention are highly satisfactory. In all cases the action commences very rapidly, that is, its effects are clearly visible from the first week on. The results are particularly satisfactory in respect of the improvement of the moisture content and elasticity of the skin tissues.

In general the clinical tests with human beings confirm that there is an active stimulation of the bio synthesis in the connective tissue of the dermis and particularly a stimulating action regarding the mitosis in the Malpighi layer and likewise a reformation of the elastin network in the intermediary dermo-epidermic zone. As a result damaged skin, be it on the basis of an injury, be it on the basis of natural aging, is imparted a thickness and elasticity quite close to the skin of young persons.

The pharmacological and pharmacodynamic tests in general have also shown that the creams, pomades, etc. of the invention do not pass beyond the superficiary layers of the dermis. Actually no modification of the myelogram or of the hemogram has been observed during the entire time of application in case of rats. This fact is of the greatest importance since it proves the difference of application of vitamin $B_{12}$ in association with a percutaneous penetration vehicle as proposed in the present invention as compared with the known action of vitamin $B_{12}$ regarding the maturing of the erythrocytes and more specifically the action regarding the hemoglobin metabolism. All this shows the critical difference of application in a purely local manner from the prior art application by general constitutional ways.

Without further analysis, the foregoing will so fully reveal the gist of the present invention that others can be applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A method for the treatment of an animal or human patient suffering from a loss of elasticity or loss of thickness of the skin or from excessive dryness of the skin due to aging of the skin, the said method comprising applying topically to the affected area of the skin an effective amount of a pharmaceutical composition comprising a homogeneous mixture of an aqueous solution of cyanocobalamin or hydroxycyanocobalamin and a pharmaceutically acceptable percutaneous penetration vehicle therefor, the said composition having a pH between about 4.0 and 7.0, being resistant to both oxidation and reduction, and being pharmaceutically acceptable for repeated application to cutaneous connective tissue over prolonged periods of time.

2. The method of claim 1 wherein the percutaneous penetration vehicle consists of a fatty skin cream.

3. A method as defined in claim 1 in which the composition contains between 1 and 100 micrograms per gram of cyanocobalamin or hydroxycyanocobalamin.

4. A method as defined in claim 1 in which the composition includes N-propionyl-epsilon-aminocaproic acid or a sodium, calcium, or magnesium salt thereof.

5. A method as defined in claim 3 in which the N-propionyl-epsilon-aminocaproic acid or a sodium, calcium or magnesium salt is present in the composition in an amount of at least 10 and at most 50 milligrams per gram.

6. A method as defined in claim 1 in which the composition includes ribonucleic acid.

7. A method as defined in claim 6 in which the ribonucleic acid is present in the composition in an amount between at least 0.25 and at most 1 milligram per gram.

8. A method as defined in claim 1 in which the composition includes chicken embryo extract prepared by extraction of chicken embryos with an aqueous solution of sodium chloride in the proportions of 1 gram of chicken embryos to 1 milliliter of the sodium chloride solution.

9. A method as defined in claim 8 in which the chicken embryo extract is present in the composition in an amount of at least 0.0005 and at most 0.05 milliliter per gram.

10. A method as defined in claim 1 in which the composition is applied topically to the affected area of the cutaneous tissue at least once daily for a period of at least 3 days.

11. A method as defined in claim 1 in which said percutaneous penetration vehicle consists of a fatty skin cream.

* * * * *